United States Patent

Abblard et al.

[11] 4,013,716
[45] Mar. 22, 1977

[54] PREPARATION OF N-ARYL-IMIDOCARBONYL UREAS

[75] Inventors: Jean Abblard, St. Didier au Mont d'Or; Pierre Poignant, Nyons, both of France

[73] Assignee: PEPRO, Societe pour le Developement et la Vente de Specialities Chimiques, Lyon, France

[22] Filed: Mar. 25, 1974

[21] Appl. No.: 454,303

[30] Foreign Application Priority Data

Mar. 27, 1973 France ............................ 73.11843

[52] U.S. Cl. .......................... 260/553 A; 71/120; 71/98; 260/501.12; 260/501.14
[51] Int. Cl.[2] ................. C07C 127/19; A01N 9/20
[58] Field of Search ............................ 260/553 A

[56] References Cited

UNITED STATES PATENTS

| | | |
|---|---|---|
| 3,146,262 | 8/1964 | Schafer et al. ............... 260/553 A |
| 3,547,937 | 12/1970 | Diana ........................ 260/553 A X |
| 3,629,455 | 12/1971 | Diana ........................ 260/553 A X |
| 3,784,582 | 1/1974 | Walls ........................ 260/553 A X |
| 3,790,631 | 2/1974 | Diana ........................... 260/553 A |
| 3,823,179 | 7/1974 | Fuchs ........................ 260/553 A X |
| 3,830,839 | 8/1974 | Diana ........................... 260/553 A |
| 3,898,277 | 8/1975 | Duerr et al. ................ 260/553 A X |
| 3,903,084 | 9/1975 | Ducharme et al. .......... 260/553 R X |
| 3,966,805 | 6/1976 | Seckinger et al. ............. 260/553 A |

FOREIGN PATENTS OR APPLICATIONS

| | | |
|---|---|---|
| 1,357,946 | 3/1964 | France |
| 2,308,943 | 9/1973 | Germany ...................... 260/553 A |
| 1,175,223 | 8/1964 | Germany ...................... 260/553 A |
| 959,997 | 6/1964 | United Kingdom |

OTHER PUBLICATIONS

"N-Phenylformadines", Duerr et al., CA 77;126259z, (1972).
"Urea derivatives as selective herbicides", Martin et al., CA 72:20787b (1970).

*Primary Examiner*—Daniel E. Wyman
*Assistant Examiner*—Thomas A. Waltz
*Attorney, Agent, or Firm*—Browdy and Neimark

[57] ABSTRACT

Compounds having herbicidal properties having the formula:

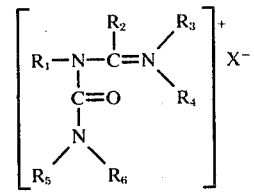

in which:
$R_1$ is a phenyl radical of the formula:

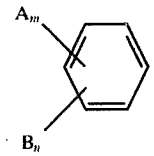

where
A is a hydrogen atom, a halogen atom, a lower alkyl of 1–5 carbons, a halogenated lower alkyl of 1–5 carbons, or an alkoxy radical, an alkylthio radical, an alkylcarbamoyloxy radical, the alkyl portion of all these radicals containing from 1 to 5 carbon atoms;
B is a phenyl radical, a phenoxy radical or a phenylthio radical which can contain from 1 to 5 halogen atoms on the nucleus, an alkyl radical containing from 1 to 5 carbon atoms or the trifulormethyl radical;
$m$ is an integer from 1 to 5; and
$n$ is 0 or 1, $m + n$ being at most equal to 5; or
$R_1$ is an alicyclic radical, the ring containing from 3 to 10 carbon atoms;
$R_2$ is a hydrogen atom, an alkyl radical containing 1 to 5 carbon atoms, an optionally substituted phenyl radical;
$R_3$ and $R_4$ are optionally substituted alkyl radicals containing from 1 to 5 carbon atoms, optionally substituted phenyl radicals;
$R_5$ and $R_6$ are alkyl radicals containing 1 to 5 carbon atoms, alkenyl or alkinyl radicals containing 2 to 5 carbon atoms, aloxy radicals containing 1 to 5 carbon atoms, cycloalkyl radicals containing 3 to 6 carbon atoms, and
X is an anion which can be either mineral, such as in particular halide, perhalide, methylsulfate; or organic, such as in particular formate, acetate or oxalate.

4 Claims, No Drawings

PREPARATION OF N-ARYL-IMIDOCARBONYL UREAS

This invention relates to substituted formamidine derivatives as new industrial products, to processes for preparing compounds of this kind, and to the use of these compounds as active ingredients in pesticidal and, more especially, herbicidal compositions.

The compounds according to the invention correspond to the formula:

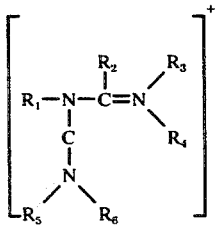

in which:

$R_1$ is a phenyl radical of the formula:

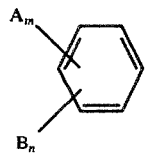

where

A is a hydrogen atom, a halogen atom, a lower alkyl of of 1–5 carbons, a halogenated lower alkyl of 1–5 carbons, or an alkoxy radical, an alkylthio radical, an alkylcarbamoyloxy radical, the alkyl portion of all these radicals containing from 1 to 5 carbon atoms;

B is a phenyl radical, a phenoxy radical or a phenylthio radical which can contain from 1 to 5 halogen atoms on the nucleus, an alkyl radical containing from 1 to 5 carbon atoms or the trifulormethyl radical;

$m$ is an integer from 1 to 5; and $n$ is 0 or 1, $m + n$ being at most equal to 5; or $R_1$ is an alicyclic radical, the ring containing from 3 to 10 carbon atoms;

$R_2$ is a hydrogen atom, an alkyl radical containing 1 to 5 carbon atoms, an optionally substituted phenyl radical;

$R_3$ and $R_4$ are optionally substituted alkyl radicals containing from 1 to 5 carbon atoms, optionally substituted phenyl radicals;

$R_5$ and $R_6$ alkyl radicals containing 1 to 5 carbon atoms, alkenyl or alkinyl radicals containing from 2 to 5 carbon atoms, alkoxy radicals containing 1 to 5 carbon atoms, cycloalkyl radicals containing 3 to 6 carbon atoms; and X is an anion which can be either mineral, such as in particular halide, perhalide, methylsulphate; or organic, such as in particular formate, acetate or oxalate.

In this group of compounds, preference is given to compounds corresponding to the formula:

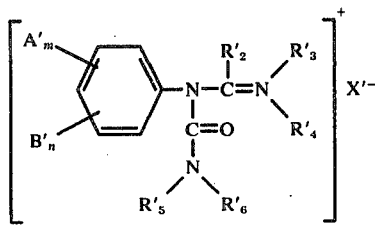

in which:

A' is hydrogen, halogen, alkyl of 1–4 carbons, trifluormethyl, methoxy or ethoxy;

$m'$ is an integer from 1 to 3; $n'$ is 0 to 1, $m' + n'$ being at most equal to 3;

B' is the 4-methylphenoxy or 4-chlorphenoxy;

$R'_2$ is hydrogen or methyl;

$R'_3$ and $R'_4$ are each a $C_1$-$C_4$-alkyl;

$R'_5$ and $R'_6$ are each a $C_1$-$C_4$-alkyl or a $C_2$-$C_4$-alkenyl;

X is a halide or methylsulphate.

The compounds according to the invention can be prepared by any one of several processes. For reasons of convenience, these processes will be described with reference to more particular reactants which lead to halides of N-phenyl-N',N'-dialkylformamidinium, although it is obvious that they can be used for the preparation of compounds according to the formula in which R is a radical other than the phenyl nucleus, while $R_3$ and $R_4$ have a meaning other than alkyl and X is an anion other than a halide.

The first process comprises reacting an optionally substituted N-phenyl-n', n'-dialkylformamidine with a N,N-disubstituted carbamoyl halide in accordance with the following scheme:

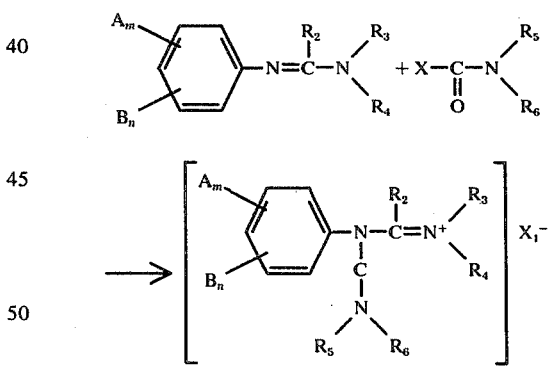

The N,N-disubstituted carbamoyl halide is introduced very slowly into the formamidine, optionally present in excess. The reaction is carried out by heating for 5 to 30 hours at a temperature of from about 50° to 150° C. Very good results have been obtained with temperatures in the range from 90° to 100° C and with reaction times of from 10 to 20 hours. Although temperatures below 90° C can be used, they necessitate a longer reaction time, whereas at temperatures above 100° C the yield is displaced in favor of, in particular, formamidine hydrochloride.

The formamidines which can be used for this reaction can be obtained by methods known per se, for example by reacting a complex of the formula:

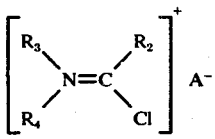

in which A is one of the radicals $PO_2Cl_2^-$, $COCl^-$, $SOCl^-$ or $SO_2Cl^-$, with an aniline optionally substituted on the nucleus (BREDERECK et al., Chem. Ber. 1959,92, page 837).

Complexes which are the most economic to use are the following:

(1) —$R_3 = R_4 = CH_3$, and $R_2 = H$
(2) —$R_2 = R_3 = R_4 = CH_3$
(3) —$R_3 = C_6H_5$, and $R_2 = R_4 = CH_3$
(4) —$R_2 = C_6H_5$, and $R_3 = R_4 = CH$ In a second process, an optionally substituted N-phenyl-n',N'-dialkyl-1-haloformamidine is reacted with an N,N-dialkylformamide used in a slight excess. The reaction, which can be carried out at ambient temperature over a period of 24 to 48 hours, or under reflux approaching 130° C over a period of a few minutes, takes place in accordance with the following scheme:

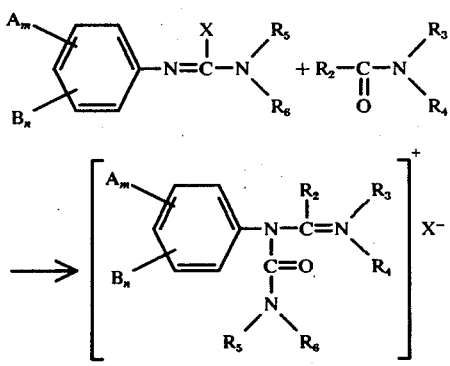

The halo-1-formamidines used for this reaction can be obtained by methods known per se by reacting a dialkylamine with an optionally substituted N-phenyl isonitrile dichloride which is itself obtained by chlorinating the corresponding formamilide (Angewandte Chemie, Int. Edition, 5 and 6, No. 8, 1967, pages 649-655).

These halo-1-formamidines can also be obtained by reacting a trisubstituted urea with phosphorus pentachloride (cf. French Pat. No. 1,243,647).

It is possible by these processes to obtain the following compounds which illustrate a group of compounds according to the invention:

1. N-phenyl-N-(N,N-dimethyl-carbamoyl)-N',N'-dimethylformamidinium halide,
2. N-(4-chlorphenyl)-N-(N,N-dimethylcarbamoyl)-N',N'-dimethylformamidinium halide,
3. [N-(3,4-dichlorphenyl)-N-(N,N-dimethylcarbamoyl) ]-N',N'--dimethylformamidinium halide,
4. [N-3,4-dichlorphenyl)-N-(N,N-dimethylcarbamoyl) ]-N',N'--methylethylformamidinium halide,
5. N-3,4-dichlorphenyl)-N-(N,N-methylpropylcarbamoyl)-N',N'-dimethylformamidinium halide,
6. N-(3,4-dichlorphenyl)-N-(N,N-methylpropylcarbamoyl)-1-methyl-N',N'-dimethylformamidinium halide,
7. N-(3,4-dichlorphenyl)-N-(N,N-methyl-n-butylcarbamoyl)-N',N'-diethylformamidinium halide,
8. N-(3,4-dichlorphenyl)-N-(N,N-methyl-n-butylcarbamoyl)-1-methyl-N, N'-dimethylformamidinium halide,
9. N-(3-chloro-4-methoxyphenyl)-N-(N,N-dimethylcarbamoyl)-N',N'-dimethylformamidinium halide,
10. N-(4-bromophenyl)-N-(N,N-dimethylcarbamoyl)-n'',N'-dimethylformamidinium halide,
11. N-(3-trifluromethylphenyl)-N-(N,N-dimethylcarbamoyl)-N',N'-dimethylformamidinium halide,
12. N-(3-trifluormethyl)-N-(N,N-dimethylcarbamoyl)-1-methyl-N',N'-dimethylformamidinium halide,
13. N-(4-trifluormethylphenyl)-N-(N,N-dimethylcarbamoyl)-N',N'-dimethylformamidinium halide,
14. N-(4-ethylphenyl)-N-(N,N-dimethylcarbamoyl)-N',N'-dimethylformamidinium halide,
15. N-(4-isopropylphenyl)-N-(N,N-dimethylcarbamoyl)-N',N'-dimethylformamidinium halide,
16. N-(4-isopropylphenyl)-N-(N,N-dimethylcarbamoyl)-N',N'-diethylformamidinium halide, 17. N-(4-isopropylphenyl)-N-(N,N-methylethylcarbamoyl)-N',N'-dimethylformamidinium halide and its N,N-methylpropyl and N,N-methyl-n-butyl homologues,
18. N (3-chloro-4-isopropylphenyl)-N-(N,N-dimethylcarbamoyl)-N',N'-dimethylformamidinium halide and its N,N-methylethyl, N,N-methylpropyl and N,N-methyl-n-butyl homologues,
19. N-(4-isopropylphenyl)-N-(N,N-dimethylcarbamoyl) N'-methylformamidinium halide,
20. N-(3-chloro-4-methylphenyl)-N-(N,N-dimethylcarbamoyl)-N',N'-dimethylformamidinium halide,
21. N-(4-tert.-butylphenyl)-N-N,N-dimethylcarbamoyl)-N', N'-dimethylformamidinium halide and its N,N-methylethyl and N,N-methylpropyl homologues,
22. N-(2-butylcarbamoyloxyphenyl)-N-(N,N-dimethylcarbamoyl)-N',N'-dimethylformamidinium halide,
23. N-(4-(4-chlorophenoxy)-phenyl)-N-(N,N-dimethylcarbamoyl) dimethylformamidinium halide,
24. N-(4-(4-methylphenoxy)-phenyl)-N-(N,N-dimethylcarbamoyl)-N',N'-dimethylformamidinium halide,
25. N-(3,4-dichlorphenyl)-N-(N,N-methyl-N-butylcarbamoyl)-N',N'-dimethylformamidinium halide,
26. N-(4-chlorphenyl)-N-(N-methyl-N-isobutinylcarbamoyl)-N',N'-dimethylformamidinium halide,
27. N-(4-chlorphenyl)-N-(N-methyl-N-methoxycarbamoyl)-N',N'-dimethylformamidinium halide,
28. N-(3,4-dichlorphenyl)-N-(N-methyl-N-methoxycarbamoyl)-N',N'-dimethylformamidinium halide,
29. N-(4-bromophenyl)-N-(N-methyl-N-methoxycarbamoyl)-N',N'-dimethylformamidinium halide,
30. N-(3-chloro-4-bromophenyl)-N-(N-methyl-N-methoxycarbamoyl)-N',N'-dimethylformamidinium halide, 31. N-cyclooctyl-N-(N,N-dimethylcarbamoyl)-N',N'-dimethylformamidinium halide,
32. N-(hexahydro-4,7-methanoindane-5-yl)-N-(N,N-dimethylcarbamoyl)-N',N'-dimethylformamidinium halide,
33. N-1 or -2-(3a, 4, 5, 6, 7, 7a-hexahydromethanoindanyl)-N-(N,N-dimethylcarbamoyl)-N',N'-dimethylformamidinium halide,
34. N-2-(benzothiazolyl)-N-methyl-N'-methyl-N'-(N,N-dimethylcarbamoyl)-formamidinium halide.

The preparation of some of these compounds is illustrated in, but by no means limited to, the following Examples which also show their herbicidal properties.

The formamidinium halides prepared were characterized by nuclear magnetic resonance spectrography (N.M.R.). The spectra were formed at 60,000 MHz in hexadeuteric DMSO with tetramethylsilane as internal reference.

Identification of the protons is represented by the field displacement δ in ppm, the letters S and M respectively denoting a singlet and a multiplet.

EXAMPLES 1 to 5

EXAMPLE 1

Preparation of N-(3,4-dichlorphenyl)-N-(N,N-dimethylcarbamoyl)-N',N'-dimethylformamidinium chloride 10.75 g (0.1 mol) of N,N-dimethylcarbamoyl chloride are introduced over a period of 12 hours at 90° C into 21.7 g (0.1 mol) of N-(3,4-dichorphenyl)-N', N'-dimethylformamidine. Forty ml of ethylacetate are added to the mixture which is then heated under reflux for 30 minutes while stirring. After cooling, the precipitate is centrifuged, washed with ethylacetate and dried. The product obtained is then recrystallized from ethylacetate.

Yield: 25%, melting point: 180° C.

The structure is confirmed by the NMR results set out in the accompanying Table.

EXAMPLE 2

Preparation of N-(4-isopropylphenyl)-N(N,N-dimethyl carbamoyl)-N',N'-dimethylformamidinium chloride 10.75 g (0.1 mol) of N,N-dimethylcarbamoyl chloride are introduced over a period of 15 hours at 90° C into 19.0 g (0.1 mol) of N-(4-isopropylphenyl)-N',N'-dimethylformamidine. The mixture solidifies. Forty ml of ethylacetate are added to it, followed by heating under reflux with stirring for 30 minutes. After cooling, the precipitate is again washed with ethylacetate and dried. The product obtained is then recrystallized from ethylacetate.

Yield: 71%, melting point: 175° C.

The structure is confirmed by the NMR results set out in the accompanying Table.

EXAMPLE 3

Preparation of N-(3-chloro-4-methylphenyl)-N-(N,N-dimethylcarbamoyl)-N',N'-dimethylformamidinium chloride Following the procedure of Example 1, 18.65 g (0.1 mol) of N-(3-chloro-4-methylphenyl)-n',N'-dimethylformamidine are reacted with 10.75 g (0.1 mol) of N,N-dimethylcarbamoyl chloride.

Yield: 65%, melting point: 175° C.

The structure is confirmed by the NMR results set out in the accompanying Table.

EXAMPLE 4

Preparation of N-(3-trifluormethylphenyl)-N-(N,N-dimethylcarbamoyl)-N',N'-dimethylformamidinium chloride Following the procedure of Example 1, 10.9 g (0.1 mol) of N-3-trifluormethylphenyl)-N',N'-dimethylformamidine are reacted with 10.75 g (0.1 mol) of N,N-dimethylcarbamoyl chloride.

Yield: 35%, melting point: 152° C.

The structure is confirmed by the NMR results set out in the accompanying Table.

EXAMPLE 5

Preparation of N-(3-chloro-4-methoxyphenyl)-N-(N,N-dimethylcarbamoyl)-N',N'-dimethylformamidinium chloride Following the procedure of Example 1, 21.25 g (0.1 mol) of N-(3-chloro-4-methoxyphenyl)-N',N'-dimethylformamidine are reacted with 10.75 g (0.1 mol) of N,N-dimethylcarbamoyl chloride Yield: 70%, melting point: 182° C.

The structure is confirmed by the NMR results set out in the accompanying Table.

EXAMPLES 6 to 11

Second process

EXAMPLE 6

Preparation of N-(3,4-dichlorophenyl)-N-(N,N-dimethylcarbamoyl)-N',N'-dimethylformamidinium chloride A mixture of 25.2 g (0.1 mol) of N-3,4-dichlorophenyl)-N',N'-dimethyl-1-chloroformamidine and 20 g (0.3 mol) of dimethylformamide is stirred for 24 hours at room temperature. The mixture solidifies. Forty ml of ethylacetate are then introduced, after which the product is centrifuged and dried.

Yield: 78%, melting point: 180° C.

The structure is confirmed by the NMR results as in Example 1.

EXAMPLE 7

Preparation of N-(3,4-dichlorophenyl)-N-(N,N-dimethylcarbamoyl)-1-methyl-N',N'-dimethylformamidinium chloride The procedure is as in the preceding Example, except that a mixture of 25.2 (0.1 mol) of N-(3,4-dichlorophenyl)-N',N'-dimethyl-1-chloroformamidine and 26.1 (0.3 mol) of dimethylacetamide is stirred for 48 hours. After stirring for 48 hours, 20 ml of boiling ethylacetate are added. The product crystallizes on cooling.

Yield: 60+, melting point: 177° C.

The structure is confirmed by the NMR results set out in the accompanying Table.

EXAMPLE 8

Preparation of N-(3,4-dichlorophyenyl)-N-(N-methyl-N-N-butyl-carbamoyl)-N',N'-dimethylformamidinium chloride A mixture of 29.4 g (0.1 mol) of N-(3,4-dichlorophenyl)-N'-methyl-N',n-butyl-1-chloroformamidine and 20 g (0.3 mol) of dimethylformamide is stirred in the same way as described in Example 6. Yield;

Yield: 60%, melting point: 135° C.

The structure is confirmed by the NMR results set out in the accompanying Table.

| | 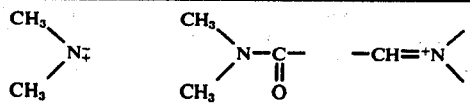 | | |
|---|---|---|---|
| Example 1 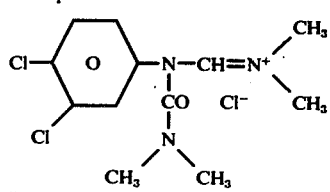 | δ = 3.13ppm (S)<br>δ = 3.61ppm (S) | δ = 2.98ppm (S) | δ = 9.01ppm (S) |
| Example 2 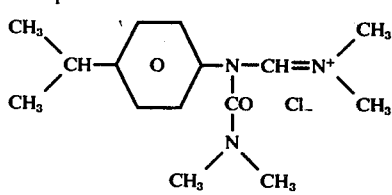 | δ = 3.13ppm (S)<br>δ = 3.61ppm (S) | δ = 2.96ppm (S) | δ = 9.08ppm (S) |
| Example 3 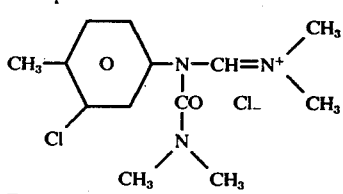 | δ = 3.13ppm (S)<br>δ = 3.60ppm (S) | δ = 2.96ppm (S) | δ = 9.06ppm (S) |
| Example 4 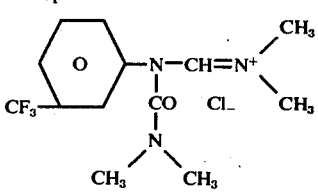 | δ = 3.15ppm (S)<br>δ = 3.65ppm (S) | δ = 3ppm (S) | δ = 9.06ppm (S) |
| Example 5 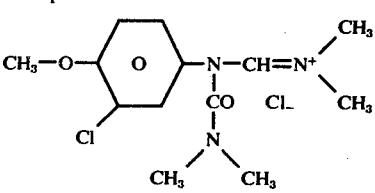 | δ = 3.08 ppm (S)<br>δ = 3.58ppm (S) | δ = 2.98ppm (S) | δ = 8.85ppm (S) |
| Example 7 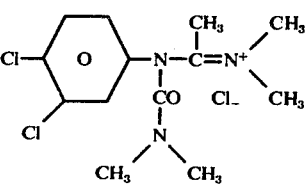 | δ = 3.25ppm (S)<br>δ = 3.60ppm (S) | δ = 2.90ppm (S) | δ = 2.48ppm (S) |
| Example 8 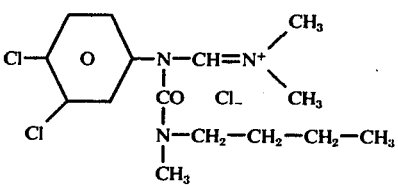 | δ = 3.15ppm (S)<br>δ = 3.63ppm (S) | $CH_3$:<br>δ = 2.93ppm (S)<br>$CH_2$:<br>δ = 3.41ppm (M) | δ = 9ppm (S) |
| | | 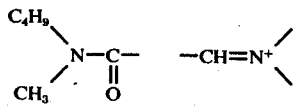 | |

EXAMPLE 9

Preparation of N-(3-trifluormethylphenyl)-N-(N,N-dimethyl-carbamoyl)-N',N'-dimethylformamidinium chloride A mixture of 25.05 g (0.1 mol) of N-(3-trifluormethyl-phenyl-N,N-dimethyl-1-chloroformamidine and 20 g (0.3 mol) of dimethylformamide is stirred in the same way as described in Example 6.

Yield: 68%, melting point: 152° C.

The structure is confirmed by the NMR results as in Example 4.

methylphenyl)-N',N'-dimethyl-1-chloroformamidine and 20 g (0.3 mol) of dimethylformamide.

Yield: 81%, melting point: 175° C.

The structure is confirmed by the NMR results as in Example 3.

EXAMPLES 12 to 28

The following Table shows the physical characteristics and the yield of other chlorides corresponding to the following general formula obtained in the same way as in Example 6. Most of these structures were confirmed by the NMR results:

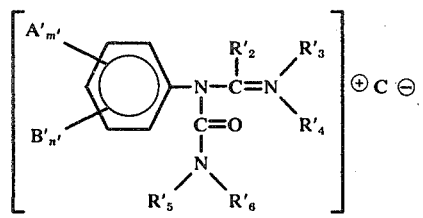

| Ex. No. | A'm',B'n' | R'$_2$ | R'$_3$,R'$_4$ | R'$_5$,R'$_6$ | Melting point | Yield |
|---|---|---|---|---|---|---|
| 12 | 3,4-Cl$_2$ | H | CH$_3$,CH$_3$ | CH$_3$,nC$_3$H$_7$ | 125° C | 30% |
| 13 | 3,4-Cl$_2$ | CH$_3$ | CH$_3$,CH$_3$ | CH$_3$,nC$_3$H$_7$ | 146° C | 60% |
| 14 | 3,4-Cl$_2$ | H | C$_2$H$_5$,C$_2$H$_5$ | CH$_3$,nC$_4$H$_9$ | 134° C | 77% |
| 15 | 3,4-Cl$_2$ | CH$_3$ | CH$_3$,CH$_3$ | CH$_3$,nC$_4$H$_9$ | 142° C | 65% |
| 16 | 4-Br | H | CH$_3$,CH$_3$ | CH$_3$,CH$_3$ | 160–1° C | 98% |
| 17 | 3-CF$_3$ | CH$_3$ | CH$_3$,CH$_3$ | CH$_3$,CH$_3$ | 163–4° C | 67% |
| 18 | 4-iso-C$_3$H$_7$ | H | C$_2$H$_5$,C$_2$H$_5$ | CH$_3$,CH$_3$ | 83° C | 60% |
| 19 | 4-iso-C$_3$H$_7$ | H | CH$_3$,CH$_3$ | CH$_3$,C$_2$H$_5$ | pasty fusion | 66% |
| 20 | 4-iso-C$_3$H$_7$ | H | CH$_3$,CH$_3$ | CH$_3$,nC$_3$H$_7$ | pasty fusion | 43% |
| 21 | 4-iso-C$_3$H$_7$ | H | CH$_3$,CH$_3$ | CH$_3$,nC$_4$H$_9$ | 97° C | 50% |
| 22 | 4-tert.-C$_4$H$_9$ | H | CH$_3$, CH$_3$ | CH$_3$,CH$_3$ | 160° C | 98% |
| 23 | 4-tert.-C$_4$H$_9$ | H | CH$_3$, CH$_3$ | CH$_3$,C$_2$H$_5$ | 148–9° C | 98% |
| 24 | 4-tert.-C$_4$H$_9$ | H | CH$_3$,CH$_3$ | CH$_3$,nC$_3$H$_7$ | 143–4° C | 98% |
| 25 | 3Cl,4-iso-C$_3$H$_7$ | H | CH$_3$,CH$_3$ | CH$_3$,CH$_3$ | 144° C | 98% |
| 26 | 3Cl,4-iso-C$_3$H$_7$ | H | CH$_3$,CH$_3$ | CH$_3$,C$_2$H$_5$ | 158° C | 98% |
| 27 | 3Cl,4-iso-C$_3$H$_7$ | H | CH$_3$,CH$_3$ | CH$_3$,nC$_3$H$_7$ | 147–8° C | 98% |
| 28 | 3Cl,4-iso-C$_3$H$_7$ | H | CH$_3$,CH$_3$ | CH$_3$,nC$_4$H$_9$ | 96° C | 98% |

EXAMPLE 10

Preparation of N-(4-isopropylphenyl)-N-(N,N-dimethylcarbamoyl)-N',N'-dimethylformamidinium chloride A mixture of 22.5 g (0.1 mol) of N-(4-isopropylphenyl)-N',N'-dimethyl-1-chloroformamidine and 20 g (0.3 mol) of dimethylformamide, of which the excess is used to solubilize the mixture, is heated under reflux for 1 minute. Forty ml of ethylacetate are then introduced, after which the product is centrifuged and dried.

Yield: 80%, melting point: 175° C.

The structure is confirmed by the NMR results as in Example 2.

EXAMPLE 11

Preparation of N-(3-chloro-4-methylphenyl)-N-(N,N-dimethylcarbamoyl)-N',N'-dimethylformamidinium chloride The procedure of the preceding Example is followed, using a mixture of 23.1 g (0.1 mol) of N-(3-chloro-4-

EXAMPLE 29

The herbicidal properties and selective properties of the compounds according to the invention were demonstrated by various tests.

For pre-emergence tests, 10 × 10 × 15 cm pots are filled with clean soil which has not been subjected to any herbicidal treatment. Seeds of various types of vegetables, the sensitivity of which to the herbicidal products to be tested it is desired to study, are placed on the soil. The seeds are then covered with a layer of soil in a thickness governed by the diameter of the seeds in accordance with usual practice. The herbicidal composition to be tested is then sprayed onto the pots.

For post-emergence tests, the same procedure is followed except that spraying is, of course, only carried out after germination when the vegetables have grown two proper leaves.

The composition is in the form of an aqueous solution obtained simply by mixing the water-soluble active material with a quantity of water calculated for spraying in the required dose per hectare.

In each of the tests, one control plant is left untreated in order to be able to verify any inhibition of growth and also to check for the possible absence of germination or for defective growth of the plants due to particular conditions.

The pots thus treated are then kept under glass under constant conditions of humidity, temperature and lighting. After 5 weeks, the results are assessed by evaluating in particular the percentage destruction of each of the species in relation to the control.

Under these conditions, it was found that:

N-(3,4-dichlorphenyl)-N-(N,N-dimethylcarbamoyl)-N',N'-dimethylformamidinium chloride (Example 1) applied in a dose of 4 kg/ha after or before emergence, completely destroys wheat (*Triticum vulgare*), maize (*Zea mays*), wild spring oat (*Avena fatua*), rye-grass (*Lolium italicum*), barnyard grass (*Echinochloa crusgalli*), lamb's quarter (*Chenopodium album*), white mustard (*Sinapis alba*) and buckwheat (*Polygonum fagopyrum*), and shows high selectivity with respect to cotton (*Gossypium hirsutum*):

N-(4-isopropylphenyl)-N-(N,N-dimethylcarbamoyl)-N',N'-dimethylformamidinium chloride (Example 2) applied in a dose of 1 kg/ha after or before emergence, completely destroys both graminaceae, such as rye-grass (*Lolium italicum*), barnyard grass (*Echinochloa crus-galli*), and black grass (*Alopecurus myosuroides*), and dicotyledons such as white mustard (*Sinapis alba*) and buckwheat (*Polygonum fagopyrum*), and is completely selective with respect to wheat (*Triticum vulgare*), rice (*Oryza sativa*), cotton (*Gossypium hirsutum*), soya (*Glycine max*), oats (*Avena sativa*), peanuts (*Arachis sp*):

N-(3,chloro-4-methylphenyl)-N-N,N-dimethylcarbamoyl)-N',N'-dimethylformamidinium chloride (Example 3) applied in a dose of 2 kg/ha after or before emergence, is perfectly selective with respect to wheat and completely destroys rye-grass, black grass, white mustard and buckwheat;

N-(3,4-dichlorophenyl)-N-(N-methyl-N-n-butylcarbamoyl)-N',N'-dimethylformamidinium chloride (Example 8), applied in a dose of 4 kg/ha after emergence, completely destroys graminaceae such as rye-grass, black grass, and dicotyledons, such as pig-weed (*Amarantus sp*), lamb's quarter, chickweed (*Stellaria media*) and buckwheat, and is perfectly selective with respect to wheat;

N-(3-trifluormethylphenyl)-N-(N,N-dimethylcarbamoyl)-N',N'-dimethylformamidinium chloride (Example 4), applied in a dose of 2 kg/ha after or before emergence, is selective with respect to maize, sorghum, and cotton, and produces at least 75% destruction of barnyard grass, black grass, lamb's quarter, lucern (*Medicago sativa*), buckwheat and chickweed;

N-(3,4-dichlorophenyl)-N-(N,N-dimethylcarbamoyl)-1-methyl-N',N'-dimethylformamidinium chloride (Example 7) applied in a dose of 2 kg/ha before or after emergence, completely destroys most weeds, including both graminaceae such as wheat, rye-grass, black grass, and dicotyledons such as in particular pig-grass, lucern, white mustard, buckwheat and chickweed;

N-(3,4-dichlorophenyl)-N-(N-methyl-N-n-butylcarbamoyl)-1-methyl-N',N'-dimethylformamidinium chloride, applied in a dose of 4 kg/ha before or after emergence, is selective with respect to wheat, maize, sorghum (*Sorghum sp*) and peas, and, before emergence, with respect to cotton, French beans (*Phaseolus vulgaris*) and sunflowers (*Helianthus annuus*), and, both in preemergence and in post-emergence treatment, reduces by at least 75% destruction barnyard grass, rye-grass, black grass, pig weed, white mustard, buckwheat and chickweed;

N-(3-trifluormethylphenyl)-N-(N,N-dimethylcarbamoyl)-1-methyl-N',N'-dimethylformamidinium chloride, applied in a dose of 2 kg/ha before or after emergence, is selective with respect to wheat, maize, sorghum, cotton and sunflower, and produces more than 75% destruction of barnyard grass, rye-grass, black grass, lamb's quarter, lucern, buckwheat and chickweed.

These tests demonstrate the advantages of the herbicidal compounds according to the present invention which, depending upon the nature of the substituents, $R_1$ to $R_6$ and the doses used, can be employed on the one hand as total herbicides and, on the other hand, as selective herbicides, before or after emergence, for such crops as, for example, cereal crops, cotton, rice, leguminosae and solanaceae, etc.

In practice, these compounds can be used in doses ranging from 0.5 to 20 kg/ha, depending upon the activity of the product, the type of treatment to be applied and the varieties and development of the crops and weeds.

For practical application, the compounds according to the invention are rarely used on their own. In general, they form part of formulations which as a rule contain a carrier or support and/or a surfactant in addition to the active material according to the invention.

In the context of the invention, a carrier or support is an organic or mineral natural or synthetic material with which the active material is associated to facilitate its application to the plant, to seeds or to the soil, or its transportation or handling. The support can be solid, e.g., clays, natural or synthetic silicates, resins, waxes, solid fertilizers, etc., of fluid, e.g., water, alcohols, ketones, petroleum fractions, chlorinated hydrocarbons, liquefied gases. Any conventionally used herbicidal carrier may be used in the present invention.

The surfactant can be an ionic or non-ionic emulsifier, dispersant, detergent or wetting agent. Examples of suitable surfactants include salts of polyacrylic acids, lignin sulphonic acids, condensates of ethylene oxide with fatty alcohols, fatty acids or fatty amines. Any conventionally used herbicidal surfactant may be used in the present invention.

The compositions according to the invention can be prepared in the form of wettable powders, soluble powders and solutions, especially aqueous solutions.

The wettable powders are normally prepared in such a way that they contain from 20 to 95% by weight of active material, and generally contain, in addition to a solid support, from 0 to 5% of a wetting agent, from 3 to 10% by weight of a dispersant, and, where necessary, from 0 to 10% by weight of one or more stabilizers and/or other additives, such as penetration or anti-lumping agents, colorants, etc.

The compositions according to the invention can contain other ingredients, for example, protective colloids, adhesives or thickeners, thixotropic agents, stabilizers or sequestrants, as well as other active materials known to have pesticidal properties, especially herbicides.

It will be obvious to those skilled in the art that various changes may be made without departing from the scope of the invention and the invention is not to be considered limited to what is described in the specification.

We claim:

1. A process for the preparation of a compound of the formula

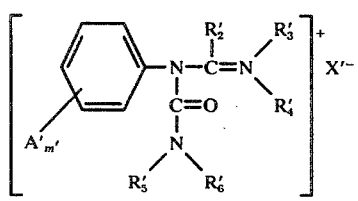

wherein

A' is H, halogen, $C_1$–$C_4$ alkyl, trifluoromethyl, methoxy or ethoxy;

m' is an integer of 1 to 3;

$R_2'$ is H or methyl;

$R_3'$ is a $C_1$–$C_4$ alkyl;

$R_4'$ is a $C_1$–$C_4$ alkyl;

$R_5'$ is a $C_1$–$C_4$ alkyl;

$R_6'$ is a $C_1$–$C_4$ alkyl; and

X' is halide comprising reacting a formamidine of the formula

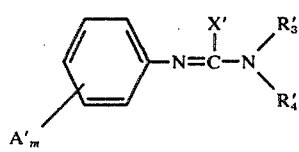

with an amide of the formula

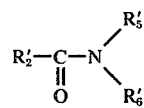

2. A process in accordance with claim 1 wherein the reaction is carried out at ambient temperature for 24–48 hours.

3. A process in accordance with claim 1 wherein the reaction is carried out under reflux for 1–20 minutes.

4. A process for the preparation of a compound of the formula

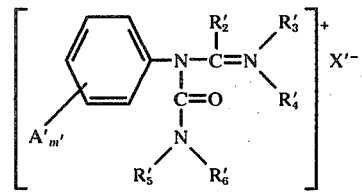

wherein

A' is H, halogen, $C_1$–$C_4$ alkyl, trifluoromethyl, methoxy or ethoxy;

m' is an integer of 1 to 3;

$R_2'$ is H or methyl;

$R_3'$ is a $C_1$–$C_4$ alkyl;

$R_4'$ is a $C_1$–$C_4$ alkyl;

$R_5'$ is a $C_1$–$C_4$ alkyl;

$R_6'$ is a $C_1$–$C_4$ alkyl; and

X' is halide comprising reacting a formamidine of the formula

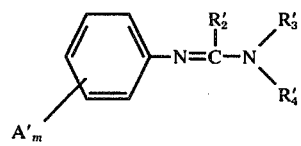

with a compound of the formula

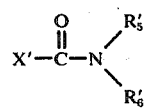

for 5–30 hours at 50°–150° C.

* * * * *